(12) United States Patent
Hashimoto et al.

(10) Patent No.: US 9,702,826 B2
(45) Date of Patent: Jul. 11, 2017

(54) METHOD OF INSPECTING A SURFACE OF AN OBJECT AND OPTICAL SYSTEM FOR PERFORMING THE SAME

(71) Applicant: SAMSUNG ELECTRONICS CO., LTD., Suwon-si, Gyeonggi-do (KR)

(72) Inventors: Kohei Hashimoto, Suwon-si (KR); Wook-Rae Kim, Suwon-si (KR); Byeong-Hwan Jeon, Yongin-si (KR); Chang-Hoon Choi, Suwon-si (KR)

(73) Assignee: SAMSUNG ELECTRONICS CO., LTD., Suwon-si, Gyeonggi-Do (KR)

( * ) Notice: Subject to any disclaimer, the term of this patent is extended or adjusted under 35 U.S.C. 154(b) by 41 days.

(21) Appl. No.: 14/751,477

(22) Filed: Jun. 26, 2015

(65) Prior Publication Data

US 2016/0077017 A1    Mar. 17, 2016

(30) Foreign Application Priority Data

Sep. 11, 2014    (KR) ........................ 10-2014-0120477

(51) Int. Cl.
| G01N 21/00 | (2006.01) |
| G01N 21/88 | (2006.01) |
| G01N 21/95 | (2006.01) |
| G01N 21/958 | (2006.01) |

(52) U.S. Cl.
CPC ..... *G01N 21/8806* (2013.01); *G01N 21/9501* (2013.01); *G01N 21/958* (2013.01); *G01N 2201/0636* (2013.01); *G01N 2201/06113* (2013.01)

(58) Field of Classification Search
CPC .......... G01N 21/8806; G01N 21/9501; G01N 21/958; G01N 2201/06113; G01N 2201/0636
USPC ...................... 356/237.1–237.6, 239.1–239.8
See application file for complete search history.

(56) References Cited

U.S. PATENT DOCUMENTS

| 6,330,059 | B1 | 12/2001 | Ishiguro et al. |
| 6,334,699 | B1 | 1/2002 | Gladnick |
| 7,319,229 | B2 | 1/2008 | Vaez-Iravani et al. |
| 7,586,604 | B2 | 9/2009 | Sharpe et al. |
| 2005/0110996 | A1* | 5/2005 | Sharpe ............... G01N 15/1436 356/338 |
| 2011/0169944 | A1 | 7/2011 | Zhao et al. |

FOREIGN PATENT DOCUMENTS

| JP | 10-068700 | 3/1998 |
| JP | 2000-131616 | 5/2000 |
| JP | 2006-090747 | 4/2006 |
| JP | 2006-268004 | 10/2006 |

* cited by examiner

*Primary Examiner* — Tri T Ton
(74) *Attorney, Agent, or Firm* — F. Chau & Associates, LLC

(57) ABSTRACT

A method of inspecting a surface of an object includes providing a laser beam irradiated in a first direction substantially parallel to the surface of the object, adjusting a diameter of the annular laser beam, reflecting the annular laser beam toward the surface of the object in a second direction substantially perpendicular to the first direction, in a primary reflection, and reflecting the primarily reflected laser toward an inspection region of the object, in a secondary reflection. An incident angle of the annular laser beam with respect to the surface of the object may be determined by the diameter of the annular laser beam.

18 Claims, 6 Drawing Sheets

METHOD OF INSPECTING A SURFACE OF AN OBJECT AND OPTICAL SYSTEM FOR PERFORMING THE SAME

CROSS-RELATED APPLICATION

This application claims priority under 35 USC §119 from Korean Patent Application No. 2014-120477, filed on Sep. 11, 2014 in the Korean Intellectual Property Office (KIPO), and all the benefits accruing therefrom, the contents of which are herein incorporated by reference in their entirety.

BACKGROUND

1. Technical Field

Exemplary embodiments are directed to a method of inspecting a surface of an object and an optical system for performing the same. More particularly, exemplary embodiments are directed to a method of inspecting a surface of a substrate using a laser, and an optical system for performing the method.

2. Discussion of the Related Art

In general, as electronic devices such as semiconductor devices, display devices, etc., have become more highly integrated, a defect such as a scratch, a foreign substance, etc., may have a small size. The defect may cause a malfunction of the electronic device. Thus, it may be useful to accurately detect the small defect.

According to related arts, a defect may be detected using a laser beam. A laser beam may be incident to a surface of an electronic device. However, the laser beam may have a large incident angle so that a small defect may not be accurately detected. Further, some defects may only be detected using a laser beam having a specific incident angle so that many defects may be missed.

SUMMARY

Exemplary embodiments provide a method of accurately inspecting a surface of an object that can accurately detect a small defect.

Exemplary embodiments also provide an optical system for performing the above-mentioned method.

According to exemplary embodiments, there may be provided a method of inspecting a surface of an object. The method includes providing a laser beam irradiated in a first direction substantially parallel to the surface of the object with an annular shape, adjusting a diameter of the annular laser beam, reflecting the annular laser beam in a second direction substantially perpendicular to the first direction toward the surface of the object, in a primary reflection, and reflecting the primarily reflected laser beam toward an inspection region of the object, in a secondary reflection. An incident angle of the annular laser beam with respect to the surface of the object may be determined by the diameter of the annular laser beam.

In exemplary embodiments, the method may further include enlarging the diameter of the laser beam, and focusing the laser beam, before providing the laser beam with the annular shape.

In exemplary embodiments, the method may further include absorbing a portion of the annular laser beam to change an incident angle of the secondarily reflected laser with respect to the inspection region of the object.

In exemplary embodiments, the object may include a semiconductor substrate, a glass substrate, etc.

In exemplary embodiments, the method may further include detecting a laser beam reflected from the inspection region of the object.

In exemplary embodiments, adjusting the diameter of the annular laser beam may include adjusting a distance between a first axicon lens and a second axicon lens.

According to exemplary embodiments, there may be provided an optical system that includes a laser source, first and second axicon lenses, a gap-adjusting member, an inclined mirror, and a parabolic mirror. The laser source may irradiate a laser beam in a first direction substantially parallel to a surface of an object. The first and second axicon lenses may provide the laser beam with an annular shape. The gap-adjusting member may adjust a distance between the first axicon lens and the second axicon lens to change a diameter of the annular laser beam. The inclined mirror may be inclined with respect to the first direction on an optical path of light reflected from the surface of the object to primarily reflect the annular laser beam in a second direction substantially perpendicular to the first direction toward the surface of the object. The inclined mirror may have a hole through which the laser beam reflected from the surface of the object may propagate. The parabolic mirror may be positioned between the surface of the object and the inclined mirror to secondarily reflect the primarily reflected laser beam from the inclined mirror toward an inspection region of the object.

In exemplary embodiments, the gap-adjusting member may be connected to the second axicon lens to change a position of the second axicon lens with respect to the first axicon lens.

In exemplary embodiments, the inclined mirror may be inclined with respect to the first direction at an angle of about 45°.

In exemplary embodiments, the optical system may further include a filter positioned between the second axicon lens and the inclined mirror to absorb a portion of the annular laser to determine a specific incident angle of the secondarily reflected laser with respect to the inspection region of the object.

In exemplary embodiments, the optical system may further include a concave lens positioned between the laser source and the first axicon lens that enlarges the diameter of the laser beam, and a convex lens positioned between the concave lens and the first axicon lens that focuses the enlarged laser beam along the first direction In exemplary embodiments, the optical system may further include a detecting unit that can detect the laser beam reflected from the inspection region of the object. The detecting unit may include an objective lens positioned between the inclined mirror and the surface of the object, an imaging lens positioned over the inclined mirror that forms an image from the laser beam propagating through the hole of the inclined mirror, and a camera positioned over the imaging lens to photograph the image.

In exemplary embodiments, the object may include a semiconductor substrate, a glass substrate, etc.

According to exemplary embodiments, there may be provided an optical system that includes a laser source, first and second axicon lenses, a filter, an inclined mirror, and a parabolic mirror. The laser source may irradiate a laser beam in a first direction substantially parallel to a surface of an object. The first and second axicon lenses may provide the laser beam with an annular shape. The filter may absorb a portion of the annular laser. The inclined mirror may be inclined with respect to the first direction on an optical path of light reflected from the surface of the object to primarily reflect the annular laser beam in a second direction substantially perpendicular to the first direction toward the surface of the object. The inclined mirror may have a hole through which the laser beam reflected from the surface of the object may propagate. The parabolic mirror may be positioned between the surface of the object and the inclined mirror to secondarily reflect the primarily reflected laser beam from the inclined mirror toward an inspection region of the object.

In exemplary embodiments, the optical system may further include a concave lens positioned between the laser source and the first axicon lens that enlarges the diameter of the laser beam, and a convex lens positioned between the concave lens and the first axicon lens that focuses the enlarged laser beam along the first direction.

In exemplary embodiments, the optical system may further include a detecting unit that can detect the laser beam reflected from the inspection region of the object. The detecting unit may include an objective lens positioned between the inclined mirror and the surface of the object, an imaging lens positioned over the inclined mirror that forms an image from the laser beam propagating through the objective lens and the hole of the inclined mirror, and a camera positioned over the imaging lens to photograph the image.

In exemplary embodiments, the optical system may further include a gap-adjusting member that can adjust a distance between the first axicon lens and the second axicon lens to change a diameter of the annular laser beam. The gap-adjusting member may be connected to the second axicon lens to change a position of the second axicon lens with respect to the first axicon lens.

In exemplary embodiments, the filter may be positioned between the second axicon lens and the inclined mirror and may determine a specific incident angle of the secondarily reflected laser beam with respect to the inspection region of the object.

According to exemplary embodiments, adjusting the diameter of the annular laser may change the incident angle of the annular laser with respect to the surface of the object. Further, a specific incident angle of the annular laser with respect to the surface of the object may be determined by absorbing a portion of the annular laser. Thus, small defects on the surface of the object may be more accurately detected.

DETAILED DESCRIPTION OF THE EMBODIMENTS

Figure 1:
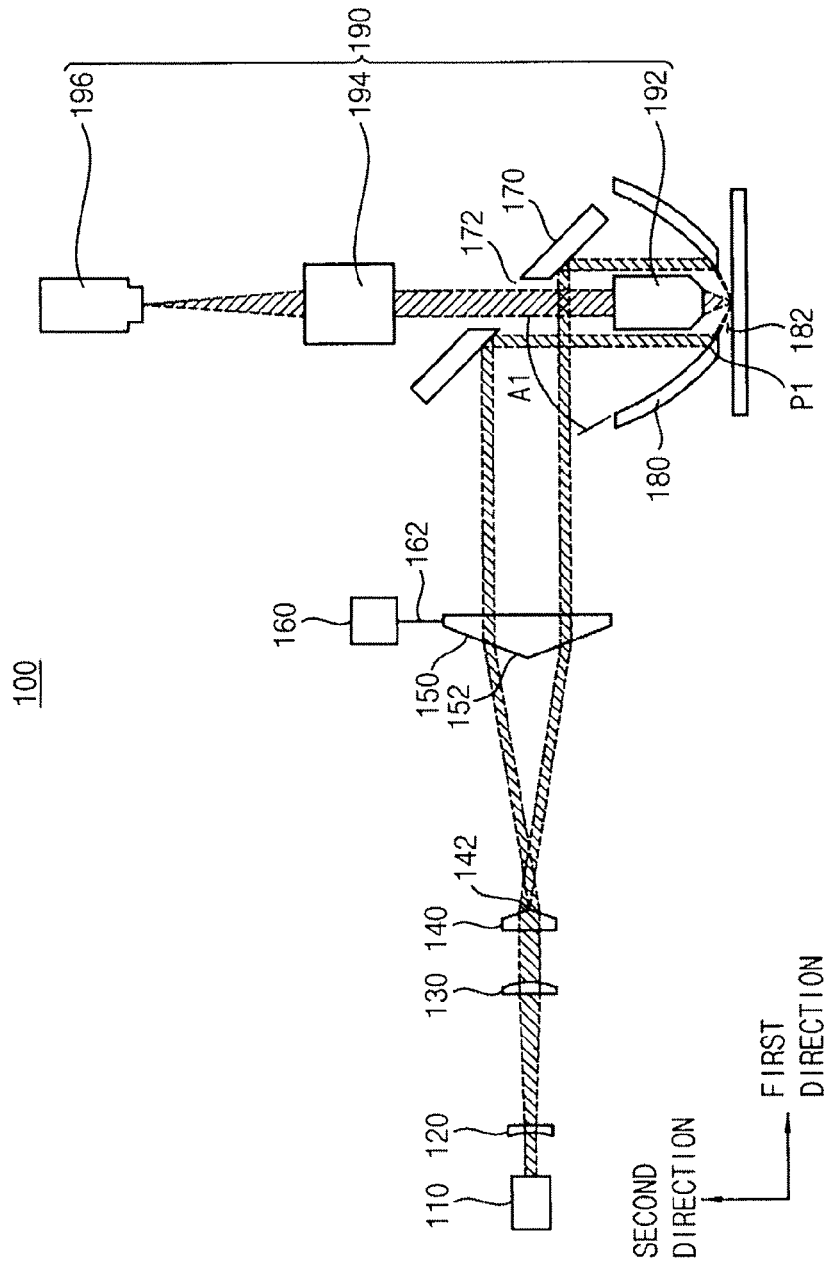
FIGS. 1 and 2 are cross-sectional views of an optical system in accordance with exemplary embodiments.

Various exemplary embodiments will be described more fully hereinafter with reference to the accompanying drawings, in which some exemplary embodiments are shown. Embodiments of the present disclosure may, however, be embodied in many different forms and should not be construed as limited to the exemplary embodiments set forth herein. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. Like numerals may refer to like elements throughout.

Hereinafter, exemplary embodiments will be explained in detail with reference to the accompanying drawings.

Optical System

Figure 2:
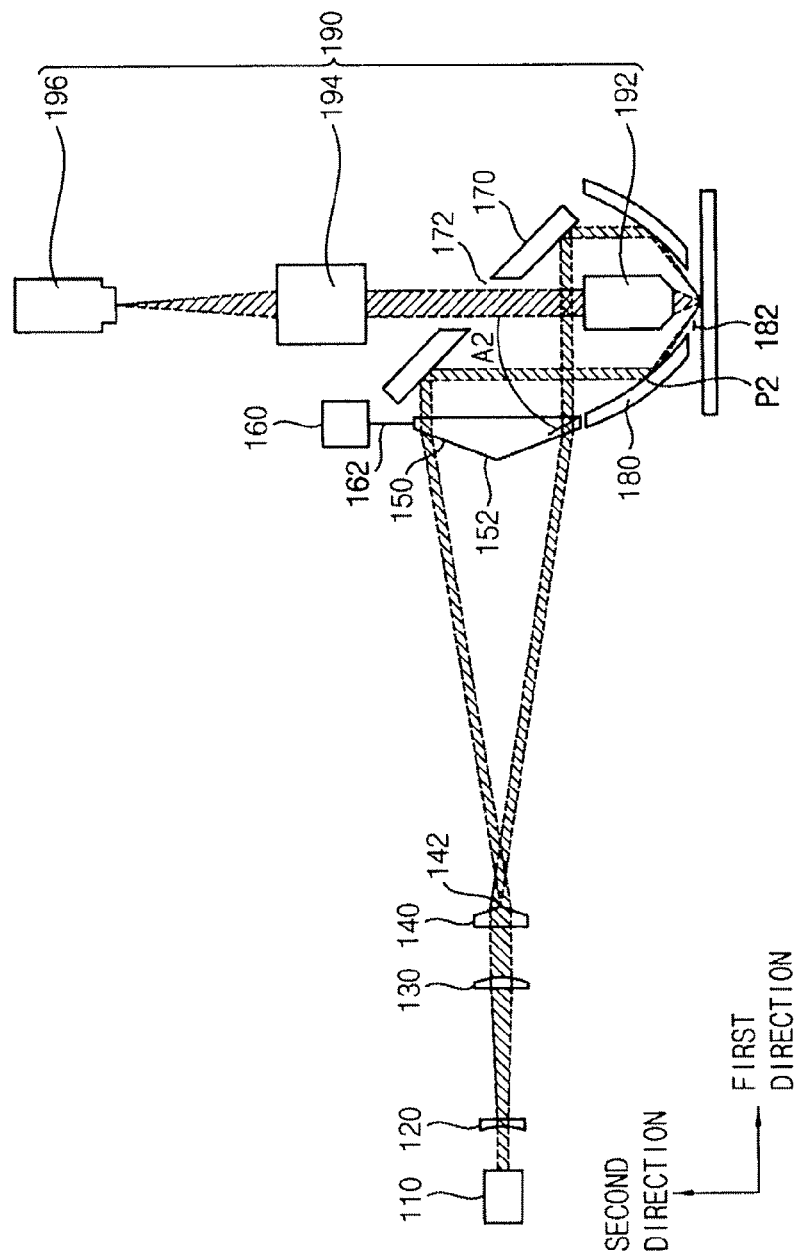
Figure 3:
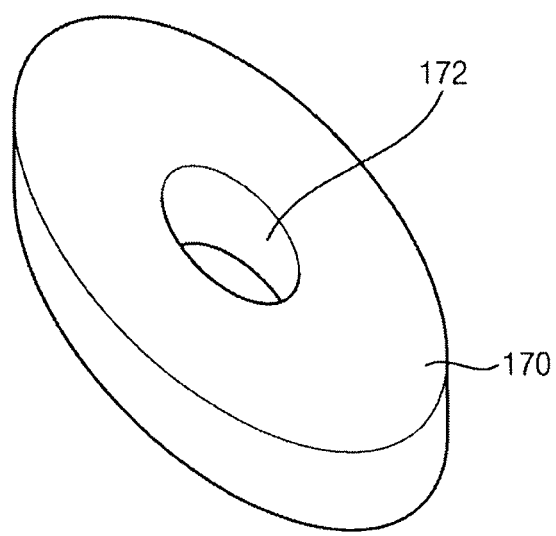
FIG. 3 is a perspective view of an inclined mirror of the optical system in FIG. 1.

FIGS. 1 and 2 are cross-sectional views of an optical system in accordance with exemplary embodiments, and FIG. 3 is a perspective view of an inclined mirror of the optical system in FIG. 1.

Referring to FIG. 1, an optical system 100 of an exemplary embodiment may include a laser source 110, a concave lens 120, a convex lens 130, a first axicon lens 140, a second axicon lens 150, a gap-adjusting member 160, an inclined mirror 170, a parabolic mirror 180 and a detecting unit 190.

The laser source 110 may irradiate a laser beam in a first direction. Thus, the first direction may correspond to a path of the laser beam. An object may have a surface substantially parallel to the first direction. The first direction may correspond to a horizontal direction. Therefore, the laser beam irradiated from the laser source 110 may propagate in the first direction substantially parallel to the surface of the horizontally disposed object. The object may include a semiconductor substrate, a glass substrate, etc.

The concave lens 120 may be positioned adjacent to the laser source 110. The concave lens 120 may be oriented in a second direction substantially perpendicular to the first direction. Thus, the second direction may correspond to a vertical direction. The concave lens 120 may diverge the laser beam irradiated from the laser source 110. Therefore, the laser beam passing through the concave lens 120 may be enlarged.

The convex lens 130 may be positioned adjacent to the concave lens 120. The convex lens 130 may be oriented in the second direction. The convex lens 130 may converge the laser beam diverged by the concave lens 120 to focus the laser beam along the first direction.

The first axicon lens 140 may be positioned adjacent to the convex lens 130. The first axicon lens 140 may have a conical portion 142 oriented toward the first direction. The conical portion 142 of the first axicon lens 140 may be oriented toward the path of the laser beam. The first axicon lens 140 may refract the laser beam focused by the convex lens 130 along the first direction to provide the laser beam with an annular cross section.

The second axicon lens 150 may be positioned spaced apart from the first axicon lens 140. The second axicon lens 150 may have a conical portion 152 opposite to the first direction. The conical portion 152 of the second axicon lens 150 may be oriented opposite to the path of the laser beam. The second axicon lens 150 may refract the annular laser beam formed by the first axicon lens 140 to focus the annular laser beam along the first direction. Thus, the laser beam irradiated from the laser source 110 may be provided with an annular shape by the first axicon lens 140 and the second axicon lens 150.

The gap-adjusting member 160 may adjust a gap or distance between the first axicon lens 140 and the second axicon lens 150. The gap-adjusting member 160 may be connected with the second axicon lens 150 via a connecting link 162. The gap-adjusting member 160 may change a position of the second axicon lens 150 with respect to the first axicon lens 140 to change the distance between the first axicon lens 140 and the second axicon lens 150. The gap-adjusting member 160 may include an actuator, such as a motor, a cylinder, etc.

A diameter of the annular laser beam may be adjusted by the gap-adjusting member 160. The annular laser beam may be refracted by the second axicon lens 150 in the first direction. Thus, the diameter of the annular laser beam may be determined based on the position of the second axicon lens 150.

Referring to FIG. 2, the gap-adjusting member 160 may move the second axicon lens 150 in the first direction. A distance between the first axicon lens 140 and the second axicon lens in FIG. 2 may be greater than a distance between the first axicon lens 140 and the second axicon lens in FIG. 1. Thus, the annular laser beam refracted by the second axicon lens 150 in FIG. 1 may have a first diameter, and the annular laser beam refracted by the second axicon lens 150 in FIG. 2 may have a second diameter greater than the first diameter. The diameter of the annular laser beam as adjusted by the gap-adjusting member 160 may determine an incident angle of the annular laser beam to the surface of the object.

The inclined mirror 170 may be inclined to the first direction. The inclined mirror 170 may reflect the annular laser beam propagating from the second axicon lens 150 toward the surface of the object. The inclined angle of the inclined mirror 170 with respect to the first direction may be about 45°. The inclined mirror 170 may be positioned over the object. Thus, the inclined mirror 170 may be positioned in an optical path of light reflected from the surface of the object. As shown in FIG. 3, to prevent interference between a laser beam reflected from the surface of the object and the inclined mirror 170, the inclined mirror 170 may have a hole 172 through which the laser beam may pass.

The parabolic mirror 180 may be positioned between the inclined mirror 170 and the object. The parabolic mirror 180 may have an opening 182 configured to expose an inspection region of the surface of the object to which the annular laser beam may be incident. The opening 182 and the hole 172 may be oriented toward the second direction.

The annular laser beam reflected from the inclined mirror 170 may be reflected from an inner surface of the parabolic mirror 180. The reflected laser beam may be incident to the inspection region of the object. An incident point of the annular laser beam on the inner surface of the parabolic mirror 180 may determine the incident angle of the annular laser beam with respect to the inspection region of the object. In FIG. 1, the first-diameter annular laser beam may be incident to a first point P1 on the inner surface of the parabolic mirror 180. The first-diameter annular laser beam may be reflected from the first point P1 of the parabolic mirror 180. The reflected laser beam may be incident to the inspection region of the object at a first incident angle A1. In contrast, in FIG. 2, the second-diameter annular laser beam may be incident to a second point P2, which may be located over the first point P1 on the inner surface of the parabolic mirror 180. The second-diameter annular laser beam may be reflected from the second point P2 of the parabolic mirror 180. The reflected laser beam may be incident to the inspection region of the object at a second incident angle A2. Because the second point P2 may be located over the first point P1, the second incident angle A2 may be less than the first incident angle A1. That is, the incident points of the annular laser beam on the inner surface of the parabolic mirror 180 may be determined by the diameter of the annular laser beam. Because the diameter of the annular laser beam may be determined by the gap between the first axicon lens 140 and the second axicon lens 150, the gap-adjusting member 150 may adjust the gap between the first axicon lens 140 and the second axicon lens 150 to determine the incident angle of the annular laser beam with respect to the inspection region of the object.

The detecting unit 190 may receive the laser beam reflected from the inspection region of the object to detect defects such as scratches, foreign substances, etc., on the surface of the object. The detecting unit 190 may include an objective lens 192, an imaging lens 194 and a camera 196. The objective lens 192 may be positioned between the surface of the object and the inclined mirror 170. The objective lens 192 may be positioned in the parabolic mirror 180. The imaging lens 194 may be positioned over the inclined mirror 170 to form an image from the laser beam passing through the objective lens 192 and the hole 172. The camera 196 may be positioned over the imaging lens 194 to photograph the image formed by the imaging lens 194.

Figure 4:
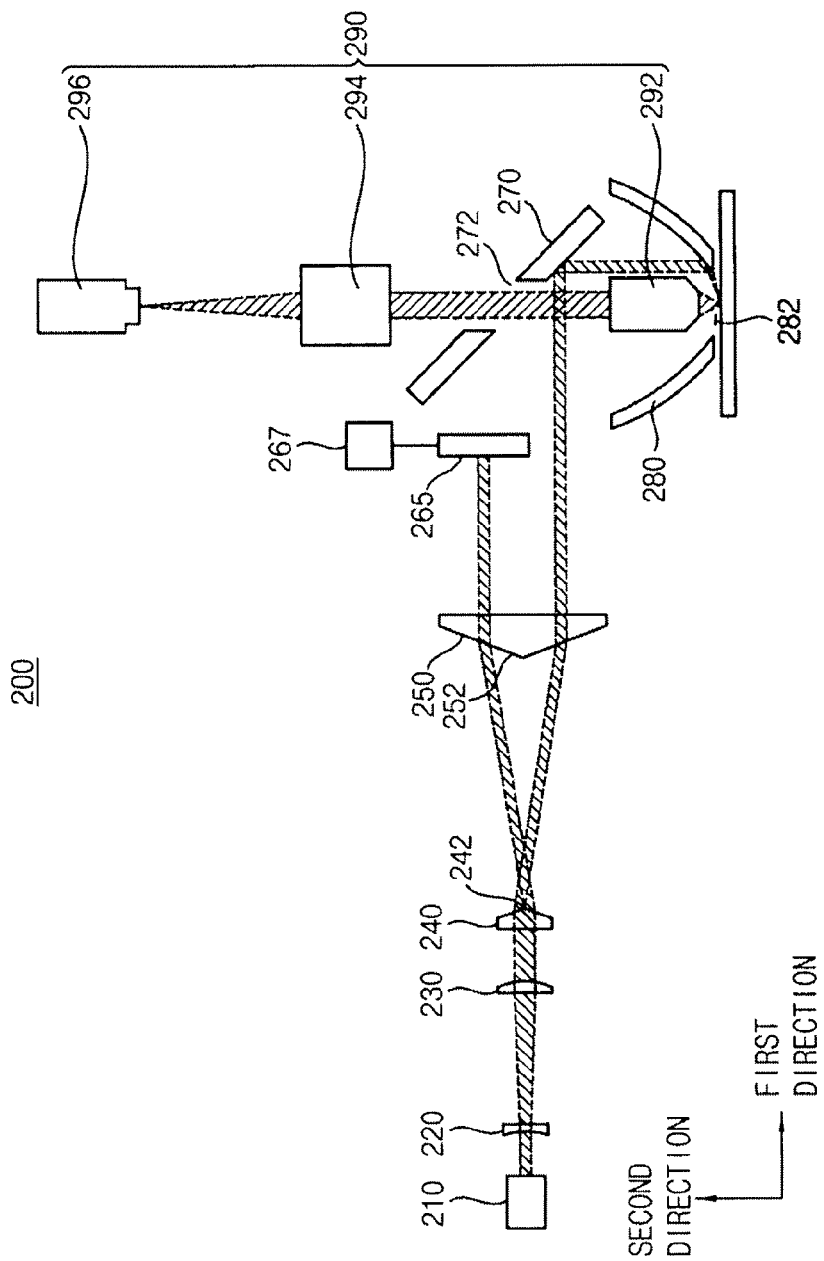
FIG. 4 is a cross-sectional view of an optical system in accordance with exemplary embodiments.

FIG. 4 is a cross-sectional view of an optical system in accordance with exemplary embodiments.

Referring to FIG. 4, an optical system 200 of an exemplary embodiment may include a laser source 210, a concave lens 220, a convex lens 230, a first axicon lens 240, a second axicon lens 250, a filter 265, an inclined mirror 270, a parabolic mirror 280 and a detecting unit 290.

The laser source 210, the concave lens 220, the convex lens 230, the first axicon lens 240, the second axicon lens 250, the inclined mirror 270, the parabolic mirror 280 and the detecting unit 290 in FIG. 4 may be substantially the same as the laser source 110, the concave lens 120, the convex lens 130, the first axicon lens 140, the second axicon lens 150, the inclined mirror 170, the parabolic mirror 180 and the detecting unit 190 in FIG. 1, respectively. Thus, any further description of the laser source 210, the concave lens 220, the convex lens 230, the first axicon lens 240, the second axicon lens 250, the inclined mirror 270, the parabolic mirror 280 and the detecting unit 290 in FIG. 4 may be omitted herein for brevity.

The filter 265 may be positioned between the second axicon lens 250 and the inclined mirror 270. The filter 265 may absorb a portion of the annular laser beam formed by the second axicon lens 250. Thus, the filter 265 may include a material for absorbing the laser beam. The filter 265 may absorb a portion of the annular laser beam to change the shape of the annular laser beam to determine the incident angle of the laser beam with respect to inspection region of the object. Here, certain defects on the surface of the object may be detected by a laser beam incident to the surface of the object at a specific incident angle. A laser beam with a specific shape provided by the filter 265 may be incident to the inspection region of the object at the specific incident angle. Thus, certain defects may be detected by a laser beam at a specific incident angle.

To change a position of the filter 265 in accordance with characteristics of a specific defect, the position of the filter 265 may be changed by an actuator 267. The actuator 267 may change the position of the filter 265 to change the shape of the annular laser beam. As a result, certain defects may be accurately detected by a laser beam incident to the inspection region at various specific incident angles.

Figure 5:
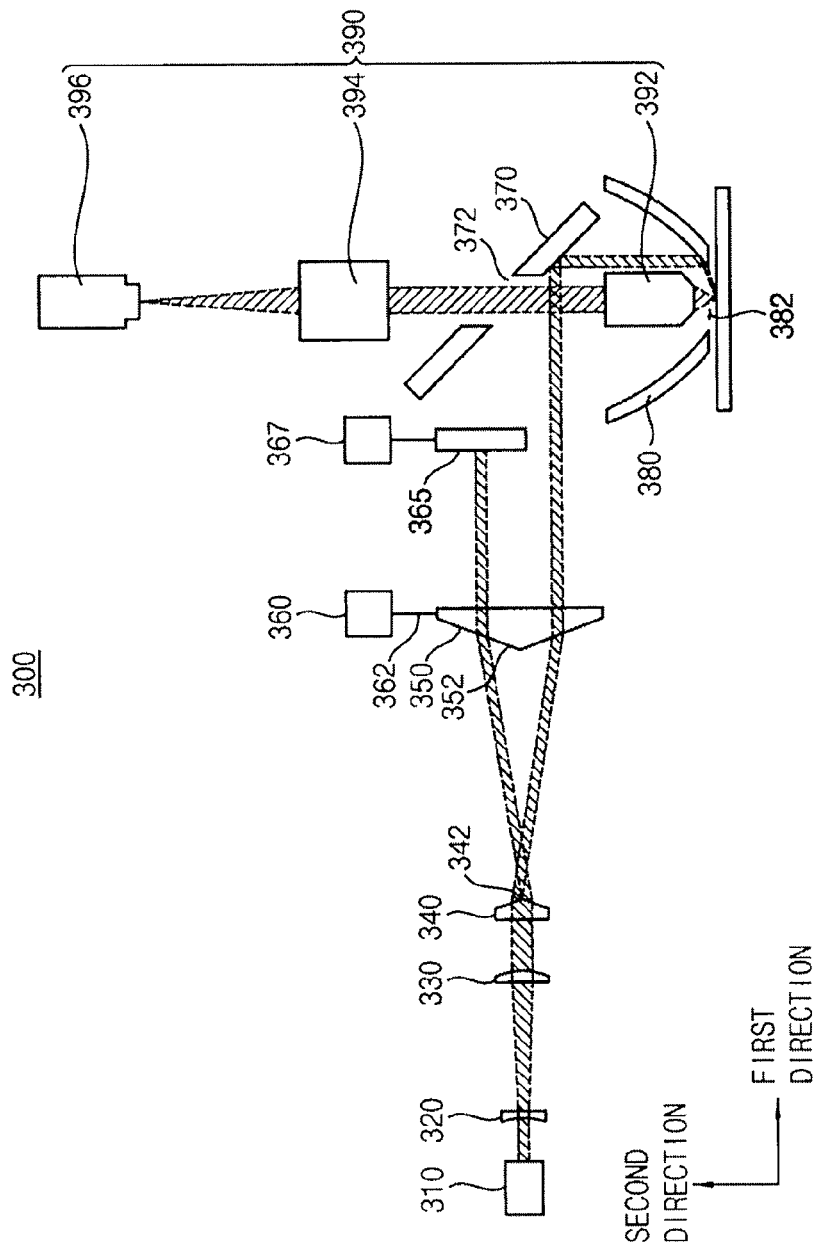
FIG. 5 is a cross-sectional view of an optical system in accordance with exemplary embodiments.

FIG. 5 is a cross-sectional view of an optical system in accordance with exemplary embodiments.

Referring to FIG. 5, an optical system 300 of an exemplary embodiment may include a laser source 310, a concave lens 320, a convex lens 330, a first axicon lens 340, a second axicon lens 350, a gap-adjusting member 360, a filter 365, an inclined mirror 370, a parabolic mirror 380 and a detecting unit 390.

The laser source 310, the concave lens 320, the convex lens 330, the first axicon lens 340, the second axicon lens 350, the inclined mirror 370, the parabolic mirror 380 and the detecting unit 390 in FIG. 5 may be substantially the same as the laser source 110, the concave lens 120, the convex lens 130, the first axicon lens 140, the second axicon lens 150, the inclined mirror 170, the parabolic mirror 180 and the detecting unit 190 in FIG. 1, respectively. Thus, any further description of the laser source 310, the concave lens 320, the convex lens 330, the first axicon lens 340, the second axicon lens 350, the inclined mirror 370, the parabolic mirror 380 and the detecting unit 390 in FIG. 5 may be omitted herein for brevity.

The optical system 300 of an exemplary embodiment may include a gap-adjusting member 360 and a filter 365. The gap-adjusting member 360 may have functions substantially similar to the functions of the gap-adjusting member 160 in FIG. 1. Furthermore, the filter 365 may have functions substantially similar to the functions of the filter 265 in FIG. 4. Thus, any further descriptions of the gap-adjusting member 360 and the filter 365 may be omitted herein for brevity.

Method of Inspecting a Surface of an Object

Figure 6:
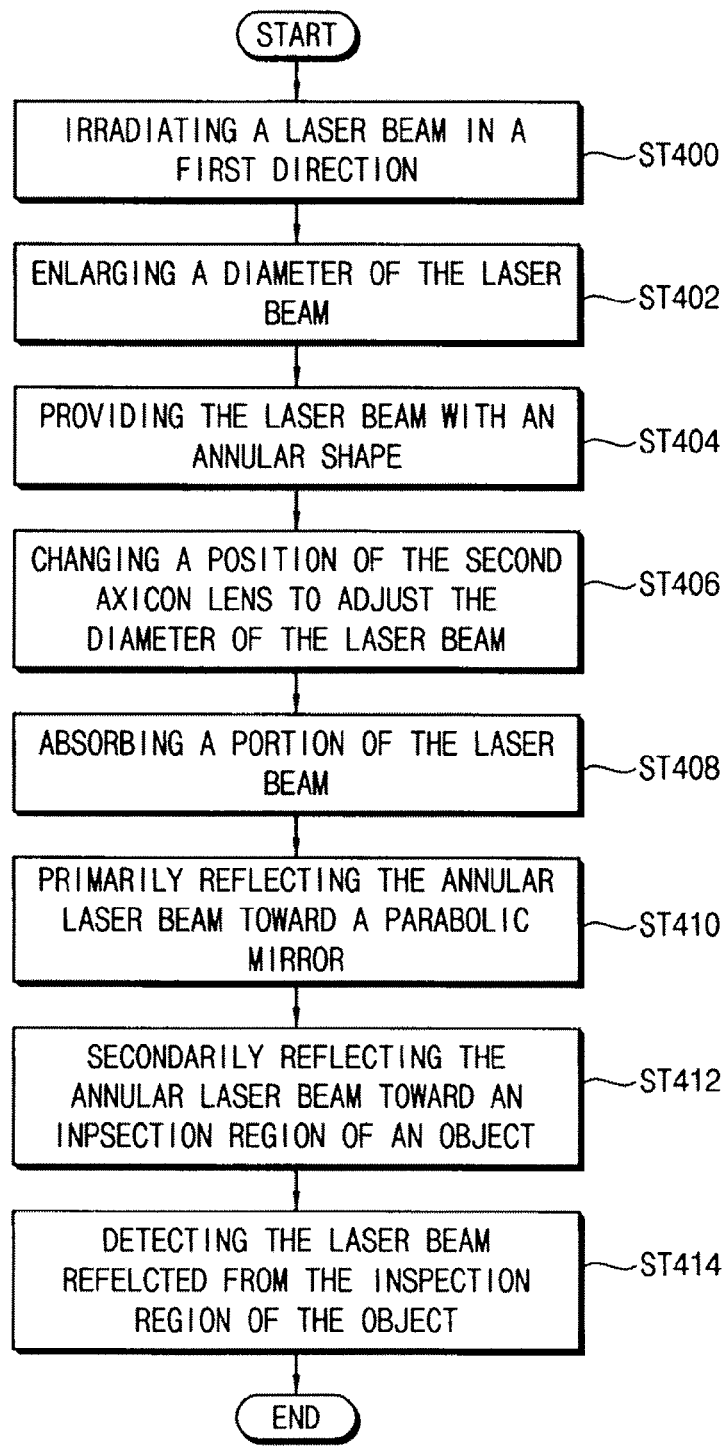
FIG. 6 is a flow chart of a method of inspecting a surface of an object using the optical system in FIG. 5.

FIG. 6 is a flow chart of a method of inspecting a surface of an object using the optical system in FIG. 5.

Referring to FIGS. 5 and 6, in step ST400, the laser source 310 may irradiate a laser beam in the first direction.

In step ST402, the concave lens 320 may diverge the laser beam to enlarge the size of the laser beam. The convex lens 330 may converge the laser beam along the first direction.

In step ST404, the first and second axicon lenses 340 and 350 may provide the laser beam with an annular shape.

In step ST406, the gap-adjusting member 360 may adjust the gap between the first axicon lens 340 and the second axicon lens 350 to change the diameter of the annular laser beam. As mentioned above, the diameter of the annular laser may determine the incident angle of the laser beam to the inspection region of the object.

In step ST408, the filter 365 may partially delete the annular laser beam. As mentioned above, a laser beam partially deleted by the filter 365 may be incident to the inspection region of the object at a specific incident angle.

In step ST410, the inclined mirror 370 may reflect the annular laser beam toward the parabolic mirror 380.

In step ST412, the annular laser beam may be reflected from the inner surface of the parabolic mirror 380. The reflected annular laser beam may be incident to the inspection region of the object. As mentioned above, the incident angle of the annular laser beam with respect to the inspection region of the object may be determined based on the reflection points on the inner surface of the parabolic mirror 380.

In step ST414, the detecting unit 390 may detect the laser beam reflected from the inspection region of the object. The laser beam reflected from the inspection region of the object may be incident to the imaging lens 394 through the objective lens 392 and the hole 372. The imaging lens 394 may form an image from the laser beam. The camera 396 may photograph the image to detect a defect on the surface of the object.

In exemplary embodiments, a method may use an optical system 300 in FIG. 5. Alternatively, a method may use an optical system 100 in FIG. 1 or an optical system 200 in FIG. 4.

According to exemplary embodiments, a diameter of an annular laser beam may be adjusted so that the annular laser beam may have various incident angles with respect to the surface of the object. Further, an annular laser beam may have a specific incident angle with respect to the surface of the object by absorbing a portion of the annular laser beam. Thus, a small defect on the surface of the object may be accurately detected.

The foregoing is illustrative of exemplary embodiments and is not to be construed as limiting thereof. Although a few exemplary embodiments have been described, those skilled in the art will readily appreciate that many modifications are possible in the exemplary embodiments without materially departing from the novel teachings of the present disclosure. Accordingly, all such modifications are intended to be included within the scope of the present disclosure as defined in the claims, and that modifications to the disclosed exemplary embodiments, as well as other exemplary embodiments, are intended to be included within the scope of the appended claims.

What is claimed is:

1. A method of inspecting a surface of an object, the method comprising:
   providing a laser beam irradiated in a first direction substantially parallel to the surface of the object with an annular shape;
   adjusting a diameter of the annular laser beam by adjusting a distance between a first axicon lens and a second axicon lens;
   reflecting the annular laser beam in a second direction substantially perpendicular to the first direction toward the surface of the object, in a primary reflection; and
   reflecting the primarily reflected laser beam to an inspection region on the surface of the object, in a secondary reflection,
   wherein an incident angle of the annular laser beam with respect to the surface of the object is determined by the diameter of the annular laser beam.

2. The method of claim 1, further comprising enlarging the diameter of the laser beam, and focusing the laser beam, before providing the laser beam with the annular shape.

3. The method of claim 1, further comprising absorbing a portion of the annular laser beam to change an incident angle of the secondarily reflected laser with respect to the inspection region of the object.

4. The method of claim 1, wherein the object comprises a semiconductor substrate or a glass substrate.

5. The method of claim 1, further comprising detecting a laser beam reflected from the inspection region of the object.

6. An optical system comprising:
   a laser source configured to irradiate a laser beam in a first direction substantially parallel to a surface of an object;
   first and second axicon lenses configured to provide the laser beam with an annular shape;
   a gap-adjusting member configured to adjust a distance between the first axicon lens and the second axicon lens to change a diameter of the annular laser beam;
   an inclined mirror inclined with respect to the first direction on an optical path of light reflected from the surface of the object to primarily reflect the annular laser beam in a second direction substantially perpendicular to the first direction toward the surface of the object, the inclined mirror having a hole through which the laser beam reflected from the surface of the object propagates; and
   a parabolic mirror positioned between the object and the inclined mirror to secondarily reflect the primarily reflected laser beam from the inclined mirror to an inspection region on the surface of the object.

7. The optical system of claim 6, wherein the gap-adjusting member is connected to the second axicon lens to change a position of the second axicon lens with respect to the first axicon lens.

8. The optical system of claim 6, wherein the inclined mirror is inclined with respect to the first direction at an angle of about 45°.

9. The optical system of claim 6, further comprising a filter positioned between the second axicon lens and the inclined mirror to absorb a portion of the annular laser beam to determine a specific incident angle of the secondarily reflected laser beam with respect to the inspection region of the object.

10. The optical system of claim 6, further comprising:
a concave lens positioned between the laser source and the first axicon lens that enlarges a diameter of the laser beam; and
a convex lens positioned between the concave lens and the first axicon lens that focuses the enlarged laser beam along the first direction.

11. The optical system of claim 6, further comprising a detecting unit configured to detect the laser beam reflected from the inspection region of the object, wherein the detecting unit comprises:
an objective lens positioned between the inclined mirror and the surface of the object;
an imaging lens positioned over the inclined mirror that forms an image from the laser beam propagating through the objective lens and the hole of the inclined mirror; and
a camera positioned over the imaging lens to photograph the image.

12. The optical system of claim 6, wherein the object comprises a semiconductor substrate or a glass substrate.

13. An optical system comprising:
a laser source configured to irradiate a laser beam in a first direction substantially parallel to a surface of an object;
first and second axicon lenses configured to provide the laser beam with an annular shape;
a filter configured to absorb a portion of the annular laser beam;
an inclined mirror inclined with respect to the first direction on an optical path of light reflected from the surface of the object to primarily reflect the annular laser beam in a second direction substantially perpendicular to the first direction toward the surface of the object, the inclined mirror having a hole through which the laser beam reflected from the surface of the object propagates;
a parabolic mirror positioned between the object and the inclined mirror to secondarily reflect the primarily reflected laser beam from the inclined mirror to an inspection region on the surface of the object; and
a gap-adjusting member configured to adjust a distance between the first axicon lens and the second axicon lens to change a diameter of the annular laser beam, wherein the gap-adjusting member is connected to the second axicon lens to change a position of the second axicon lens with respect to the first axicon lens.

14. The optical system of claim 13, wherein the inclined mirror is inclined to the first direction at an angle of about 45°.

15. The optical system of claim 13, further comprising:
a concave lens positioned between the laser source and the first axicon lens that enlarges a diameter of the laser beam; and
a convex lens positioned between the concave lens and the first axicon lens that focuses the enlarged laser beam along the first direction.

16. The optical system of claim 13, further comprising a detecting unit configured to detect the laser beam reflected from the inspection region of the object, wherein the detecting unit comprises:
an objective lens positioned between the inclined mirror and the surface of the object;
an imaging lens positioned over the inclined mirror that forms an image from the laser beam propagating through the objective lens and the hole of the inclined mirror; and
a camera positioned over the imaging lens to photograph the image.

17. The optical system of claim 13, wherein the filter is positioned between the second axicon lens and the inclined mirror and determines a specific incident angle of the secondarily reflected laser beam with respect to the inspection region of the object.

18. The optical system of claim 13, wherein the object comprises a semiconductor substrate or a glass substrate.

* * * * *